United States Patent [19]

Goldberg et al.

[11] Patent Number: 4,965,253

[45] Date of Patent: Oct. 23, 1990

[54] VISCOELASTIC MATERIAL FOR OPHTHALMIC SURGERY

[75] Inventors: Eugene P. Goldberg; Moshe Yalon, both of Gainesville, Fla.

[73] Assignee: University of Florida, Gainesville, Fla.

[21] Appl. No.: 108,068

[22] Filed: Oct. 14, 1987

[51] Int. Cl.$^5$ ............................................. A61K 31/00
[52] U.S. Cl. ........................................ 514/54; 424/80; 604/28; 604/294; 514/912; 514/913; 514/915
[58] Field of Search ................. 514/54, 912, 913, 915; 523/105; 604/28, 294; 424/80

[56] References Cited

U.S. PATENT DOCUMENTS

| | | | |
|---|---|---|---|
| 4,003,991 | 1/1977 | Krohn et al. | 424/81 |
| 4,136,173 | 1/1979 | Pramoda et al. | 514/15 |
| 4,141,973 | 2/1979 | Balazs | 514/54 |
| 4,328,803 | 5/1982 | Pape | 514/54 |
| 4,486,416 | 12/1984 | Soll et al. | 514/54 |
| 4,604,217 | 8/1986 | Lukach et al. | 523/130 |

FOREIGN PATENT DOCUMENTS 8600079  1/1986  World Int. Prop. O. ............ 514/54

*Primary Examiner*—Ronald W. Griffin
*Assistant Examiner*—Everett White
*Attorney, Agent, or Firm*—Kerkam, Stowell, Kondracki & Clarke

[57] ABSTRACT

An ophthalmic surgical procedure wherein the anterior or posterior chamber of the eye is filled with viscoelastic space-filling and ocular tissue protective surgical material, the improvement comprising the utilization therein of a composition particularly adapted for use as an ophthalmic viscoelastic surgical material in the anterior or posterior chamber of the eye consisting of an aqueous solution containing from about 1.5% to about 25%, by weight, of a physiologically acceptable, water-soluble polyvinylpyrrolidone polymer or polyvinylpyrrolidone copolymer, having a molecular weight greater than 500,000, said aqueous solution having a viscosity greater than about 5,000 centipoises, measured at 25° C. using a Brookfield viscometer.

19 Claims, No Drawings

VISCOELASTIC MATERIAL FOR OPHTHALMIC SURGERY

BACKGROUND OF THE INVENTION

1. Field of the Invention

The present invention relates to novel viscoelastic viscosurgical materials and ophthalmic surgical techniques utilizing the materials.

2. Prior Art

In ophthalmic surgical procedures such as intraocular lens implantation, cataract surgery, retinal detachment repair, etc., there exists a need for viscous, gel-like compositions to fill the chambers of the eye to protect sensitive tissue such as the corneal endothelium from trauma. See U.S. Pat. No. 4,141,973; Pruett et al, Arch. Ophthalmol., 97:2325 (1979); Holmberg et al, Ophthalmology, 91:45 and 53 (1984); Pape et al, Ophthalmology, 87:669 (1980); MacRae et al, Am. J. Ophthalmol., 95:332 (1983); and Miller et al, Annals Ophthalmol., 13:811 (1981).

The most commonly employed materials are solutions of hyaluronic acid (HA), chondroitin sulfate (CS) and methylcellulose (MS); HA being the most widely used. However, HA is extrememly expensive. Furthermore, it requires extraordinary purification to remove as much proteinaceous immunogenic material as possible but still may provoke immune reactions in some patients. The use of HA and all other currently available viscosurgical materials for ophthalmic surgery is also often accompanied by significant undesirable intraocular pressure (IOP) rise which necessitates washing from the eye at the end of surgery and may also require antiglaucoma therapy. Even though HA is normally irrigated from the eye following its use in ocular surgery, transient potentially hazardous episodes of IOP rise have been known to occur.

Sterilization and shelf-life stability are other problems associated with HA and other currently available materials. They are subject to significant degradation by thermal or radiation sterilization methods making safe sterile processing difficult and expensive. Ambient temperature instability also necessitates refrigerated shipment and storage. In contrast, the materials of the present invention are far more stable, may be readily autoclave sterilized without degradation and may be stored at room temperature safely for long periods of time.

It has also been suggested to employ an aqueous solution of high molecular weight carboxymethylcellulose (CMC) as a viscosurgical material. U.S. patent application Ser. No. 903,445, filed Sept. 4, 1986, discloses the use of a solution of high molecular weight carboxymethylcellulose as an ophthalmic viscoelastic surgical material. Although CMC represents a significant improvement over other known viscosurgical materials, especially in ease of purification and lower cost, its use may still be accompanied by some transient IOP rise following surgery.

It is an object of the present invention to provide improved ophthalmic viscoelastic surgical materials and ophthalmic surgical techniques embodying same which are far less subject to the above-noted disadvantages.

SUMMARY OF THE INVENTION

The present invention embodies a composition particularly adapted for use as an ophthalmic viscosurgical material or a synthetic vitreous material for use in the anterior chamber or posterior chamber of the eye consisting essentially of an aqueous solution preferably having a near physiological pH and osmolarity and containing at least about 1.5%, by weight, of a water soluble physiologically acceptable polyvinylpyrrolidone (PVP) or copolymer thereof, having a molecular weight greater than about 500,000, the aqueous solution having a viscosity greater than about 5,000 centipoises.

The invention further embodies an improved ophthalmic viscosurgical procedure wherein the anterior chamber of the eye is filled with a space-filling corneal endothelium and ocular tissue protective surgical material, the improvement comprising the utilization of an ophthalmic surgical material having the above described composition.

DETAILED DESCRIPTION OF THE INVENTION

The below-listed terms are employed throughout the specification and claims and they are defined as follows:

(1) "Viscoelastic" material refers to certain viscous solutions or compositions having the requisite viscous gel-like properties which enable their use to fill the anterior chamber of the eye.

(2) "Viscosurgical" material or technique refers to the viscoelastic surgical materials inserted in the eye or the surgical techniques employed to fill the anterior chamber of the eye during cataract, lens implant, etc., surgeries.

(3) "PVP" as used herein refers to any water soluble physiologically acceptable polyvinylpyrrolidone.

(4) "Physiologically acceptable" is employed to refer to materials which, when in contact with tissues in the body, are not harmful thereto. For example, the term is used to define the media in which the PVP is dissolved to form the viscoelastic material. The term is intended in this context to define aqueous solutions which are approximately isomolar with the physiological environment of the eye. Generally such media have an osmolarity of the order of 250–300 and are buffered to maintain a pH of from about 7.0 to 7.5, although osmolarity and pH may be varied substantially and for the PVP solutions of this invention simple aqueous solutions which may not be iso-osmolar may often be clinically useful.

The present invention is predicated on the discovery that solutions of physiologically acceptable polyvinylpyrrolidone (PVP) having the molecular weight, concentrations and viscosities set forth above are unexpectedly superior to solutions of PVP having properties outside these critical ranges as well as solutions of other agents when employed as ophthalmic viscosurgical materials in the anterior chamber of the eye both as a viscoelastic space filler and protector for the surrounding sensitive tissue therein during intraocular surgery.

It is essential to the invention to use PVP solutions having concentrations no lower than about 1.5% by weight, and viscosities no lower than about 5,000 centipoise in order to obtain the following balance of properties required of a practical viscosurgical material in the eye, i.e.:

(a) Readily injectable with non-Newtonian viscosity (shear thinning);

(b) Gel-like high viscosity at low shear (>5,000 cps) to insure no loss by leakage through wound opening and to enable gentle tissue manipulation;

(c) Lubricating and non-adhesive protection of endothelium, iris and other tissue from contact with the implant and instruments;
(d) Easily irrigated out of the A.C. after surgery;
(e) No significant inflammatory response or increase in intraocular pressure (IOP) with use; and
(f) Clearance from the eye of residual material.

The compositions of the invention exhibit excellent shear dependent non-Newtonian rheological properties, maintain the anterior chamber, and are easy to inject, manipulate and visualize and are non-pyrogenic and non-toxic. They also exhibit gel-like viscoelastic solution properties and biocompatibility which make them suitable for application as synthetic vitreous materials.

Polyvinylpyrrolidone offers unique advantages over previously employed ophthalmic viscoelastic materials. The material is extremely stable thereby enabling procedures such as autoclave sterilization without degradation of the product as is often the case with other materials conventionally used for ophthalmic viscoelastic applications. Its inordinate stability also contributes to its substantially indefinite shelf-life at room temperature after sterilization whereas presently employed materials require refrigeration after sterilization.

Furthermore, it has been found that introduction of the PVP ophthalmic viscoelastic material of the present invention into the eye gives rise to substantially less intraocular pressure rise as compared with products presently available in the marketplace.

Finally, PVP is a low cost material that can be prepared in very pure form since it is produced from a simple liquid monomer which is readily available in substantially pure form.

It will be understood by those skilled in the art that although gamma radiation polymerized PVP of high molecular weight is preferred, any substantially pure PVP material satisfying the above noted concentration, viscosity and molecular weight parameters may be employed in the practice of the invention and that the PVP may be prepared according to any suitable process for the preparation thereof.

Although high molecular weight commercially available PVP such as BASF Corp. or GAF Corp. PVP-K90 may be used, it is a preferred embodiment of this invention to use PVP made by gamma-radiation polymerization of aqueous PVP monomer (NVP). Such gamma-PVP materials exhibit improved viscoelastic solution properties for ophthalmic surgery and are more readily obtainable in higher purity and at lower cost.

Commercially available high mol. wt. PVP or gamma-PVP which is preferred may be dissolved in any physiologically acceptable solution having a physiologically acceptable pH and osmolarity, such as sterile water, saline or buffered saline.

It is essential that the PVP have a mol. wt. above about 500,000. There is no practical upper limit for the mol. wt. so long as the solution has the concentration of PVP and viscosity specified above The upper limit for the concentration will depend, of course, upon the mol. wt of the PVP and the desired viscosity thereof greater than about 5,000 centipoises. Generally, an upper limit of about 25%, by weight, is practical. Preferably, concentrations of 5 to 15 weight % provide optimum results for gamma-PVP having mol. wt. greater than 1,000,000.

It will be understood by those skilled in the art that by "opthalmic surgical or surgery" is meant any intraocular surgery such as intraocular lens implantation, cataract surgery, corneal transplant surgery, glaucoma surgery, retinal detachment repair, vitreous replacement, etc. The compositions of the invention are suitable for utilization in any of these ophthalmic surgical techniques.

An important advantage associated with the use of PVP is that, unlike hyaluronic acid or chondroitin sulfate, it is not derived from a proteinaceous source and has virtually no protein associated therewith. Accordingly, the use of PVP does not involve the danger of foreign protein induced immunogenic activity and does not require the extensive and costly purification procedures required for HA and CS. It also exhibits far greater chemical stability than other viscosurgical materials used heretofore and is therefore readily autoclave sterilized.

The following method is particularly preferred for preparing the PVP material, however, since the product thereof is especially adapted for ophthalmic viscoelastic applications. More specifically, the method involves gamma-irradiation induced polymerization of N-vinylpyrrolidone (NVP), alone or with comonomers, in an aqueous solution under the following preferred conditions:

(a) monomer concentration in the range of from about 0.5 to about 50% by weight;
(b) total gamma dose in the range of from about 0.01 to about 0.50 Mrad;
(c) gamma dose rate in the range of from about 10 to about 2500 rads/minute; and
(d) achieving a molecular weight for the PVP polymer greater than about 500,000.

Optimally, the method may also be carried out under one or more of the following conditions:

(e) substantially excluding free oxygen from the aqueous polymerization solution; and
(f) including a free radical scavenger in the aqueous polymerization solution.

Each of the above-described process conditions and parameters may be varied within the ranges indicated below to produce process conditions which are particularly advantageous for the PVP polymers of this invention.

(a) Monomer concentration: Increasing monomer concentration increases the polymer mol. wt. in the polymerization solution. For example, in the range of from about 3-15% NVP the PVP viscosity molecular weight increases from 560,000 to 2,700,000. However, this effect is sensitive to dose rate and total dose. For example, at 1-10% NVP, but at a lower dose rate of 64 rads/min, the mol. wt. increases from 400,000 to 4,590,000.

In general, monomer concentrations in the range 0.5-50% are preferred depending on other parameters. For example, below 0.5%, even at low dose rate and high dose, polymerization is inefficient. At monomer concentrations greater than 20-30%, effective polymerization without solution polymer gelation requires low doses and use of free radical scavengers.

(b) Dose: In general, increasing total gamma dose increases the mol. wt. of the polymer. At higher doses, lower dose rates, and higher monomer concentrations, reaction media become extremely viscous or form gels which are more difficult to dilute or dissolve, (e.g., above 0.25 Mrad and 10% NVP at 309 rads/min).

(c) Dose rate: Decreasing dose rate increases PVP mol. wt., e.g., from 1,150,000 to 5,090,000 at 10%

NVP and 0.1 Mrad as dose rate decreases from 1235 to 49 rads/min.

(d) Solution Polymer Mol. Wt.: Molecular weights greater than 5,000,000–10,000,000 are readily prepared and are operable for the purpose of the present invention.

(e) Degassing: Removal of oxygen from the solutions by vacuum and/or inert gas (e.g., argon purging) has an important effect: lower total doses are required (practical polymerization at less than 0.1 mrad). Oxygen degassing also has a large effect on PVP mol. wt. and % conversion of monomer. For example, with degassing, good polymerization is achieved at 0.05 Mrad and 10% NVP. Without degassing, polymerization is inefficient under these conditions.

(f) Free-Radical Scavengers: Free radical traps, usually reducing agents such as $Cu^+$, $Fe^{+2}$ ascorbic acid, etc., are known to inhibit radical polymerization in solution and thus be effective (especially at high gamma doses, high dose rates, and high monomer concentrations) in slowing the onset of solution gelation or cross-linking during polymerization. However, under practical polymerization conditions, this may result in lower mol. wts., high concentrations of unreacted monomer, and broad mol. wt. distributions. Also, the use of metal salts may be objectionable where maximum biocompatibility is critical.

It will be understood by those skilled in the art that the PVP of this invention may be modified by copolymerization of NVP with various neutral or ionic monomers which do not substantially affect the adaptability of the resulting polymer or ophthalmic viscoelastic applications. For example, copolymerization incorporating vinylsulfonic acids or vinylcarboxylic acids such as acrylic acid, crotonic acid or methcrylic acid can afford anionic PVP copolymer materials. Similarly, copolymerization incorporating amino-functional monomers, e.g., vinylpyridines, aminostyrenes, aminoacrylates, or aminomethacrylates such as dimethylaminoethylmethacrylate, or dimethlaminostyrenes afford cationic PVP copolymers. Applicable neutral comonomers include for example, water soluble hydroxylated acrylic monomers, acrylamide, dimethylacrylamide, ethylene oxide, vinyl derivatives of polyethylene oxide, etc.

Amounts of such co-monomers up to about 50 mol. % of the total monomer weight may be employed, it being understood that the critical process parameters listed above be maintained, e.g., total monomer concentration, molecular weight, etc.

It will also be understood by those skilled in the art that the PVP of this invention may be used in admixture in any other viscosurgical materials used in ophthalmology. The PVP solutions of this invention are compatible with HA, chondroitin sulphate and CMC for example and such PVP-HA, PVP-CMC, PVP-CS or mixtures exhibit favorable combinations of rheology, stability and biocompatibility for ophthalmic viscosurgical applications.

EXAMPLE 1

This example illustrates the important effects which result from varying the above-discussed process conditions and polymerization parameters for gamma-irradiated polymerization of NVP.

The solution PVP samples were evaluated for molecular weight by viscosity measurement ($M_v$) or gel permeation chromatography ($M_w$). For $M_v$, PVP was dissolved in distilled water and intrinsic viscosity, $[\eta]$, was measured at 30° C. in a capillary viscometer.

The results are set forth in the following tables.

TABLE 1

| Dose Rate Effect on Solution Polymer Molecular Weight For γ-Polymerized NVP | | |
| --- | --- | --- |
| Concentration: | 10% NVP in $H_2O$ | |
| Total Dose: | 0.1 Mrad | |
| Dose Rate (rads/min) | $[\eta]$ | Mol. Wt. ($M_v$) ($\times 10^6$) |
| 1235 | 1.48 | 1.15 |
| 309 | 2.21 | 2.27 |
| 137 | 2.61 | 3.04 |
| 77 | 2.85 | 3.49 |
| 49 | 3.56 | 5.09 |

The effect of dose rate was evaluated by PVP solution viscosity measurements. These results show that the molecular weight increased as dose rate decreased due to the reduced rate of initiation of radicals and the increased time of polymerization while maintaining the same total absorbed dose. At the lowest dose rate in this experiment, 49 rads/min (at 10Δ from the cobalt-60 gamma source) the highest molecular weight PVP polymer, $M_v = 5.09 \times 19^6$, was obtained.

TABLE 2

| Total Dose Effect on Molecular Weight of γ-Polymerized NVP | | |
| --- | --- | --- |
| Concentration: | 10% NVP in $H_2O$ | |
| Dose Rate: | 309 rads/min | |
| Total Dose (Mrads) | $[\eta]$ | Mol. Wt. ($M_v$) ($\times 10^6$) |
| 0.05 | 1.86 | 1.69 |
| 0.10 | 2.21 | 2.27 |

Table 2 shows the effect of total γ-irradiation dose on molecular weight at 309 rads/min. Increasing the total dose gives a higher molecular weight.

TABLE 3

| Molecular Weight of γ-Polymerized PVP at Different Monomer Concentrations | | |
| --- | --- | --- |
| Total Dose: | 0.1 Mrad | |
| Dose Rate: | 64 rads/min. | |
| NVP Concentration (%) | $[\eta]$ | Mol. Wt. ($M_v$) ($\times 10^6$) |
| 1 | 0.79 | 0.40 |
| 3 | 1.65 | 1.38 |
| 5 | 2.23 | 2.30 |
| 10 | 3.35 | 4.59 |

These results show the relationship between the concentration of NVP monomer and molecular weight of PVP at a dose rate of 64 rads/min.

The molecular weight of PVP increases significantly with increasing concentration of NVP monomer.

EXAMPLE 2

The following experiment demonstrates the very significant influence of oxygen on gamma induced PVP polymerization and the beneficial effects of carrying out polymerizations in the substantial absence of oxygen.

Gamma radiation induced polymerization of NVP was carried out in 10% NVP aqueous solution as follows:

(a) polymerization in presence of oxygen (air);

(b) polymerization in absence of oxygen using argon degassing; and
(c) polymerization in absence of oxygen using a freeze-thaw (FT) degassing method.

To determine the oxygen degassing effects on gamma radiation polymerization, monomer conversions and molecular weights were determined for NVP solutions irradiated at different doses and dose rates.

A method used for determining unreacted NVP after irradiation was as follows: 5 ml of the gamma irradiated NVP solution was extracted using 50 ml acetonitrile. NVP is soluble in acetonitrile but PVP is not. The PVP precipitate was centrifuged and the supernatant solution was analyzed for NVP. The NVP monomer solution (10% NVP/aqueous) was used as a control. NVP analysis was as follows. The 10% by weight aqueous solution was diluted with acetonitrile to appropriate concentrations (0.5 μg/ml to 5.0 μg/ml. The U.V. absorbance was measured for each solution at 323 nm to develop a standard curve of NVP concentration vs. U.V. absorbance. The regression coefficient was 0.99 for this curve. GPC was used for molecular weight measurements.

The % NVP conversion (amount of monomer reacted) is significantly affected by Ar purge deoxygenation and by FT oxygen degassing. At the very low dose of 0.01 Mrad little polymerization occurs in the non-degassed oxygen (air) containing solutions. However, 46% and 63% conversion to PVP occurred for the Ar-purged and FT samples, respectively. Even at 0.10 Mrad, samples irradiated in air showed only 90% conversion (10% unreacted NVP monomer) compared to virtually complete conversion (99%) for oxygen degassed systems. This is important for biocompatible materials where unreacted monomers can cause serious adverse toxicological behavior.

PVP molecular weight as well as monomer conversion are affected by oxygen degassing. The Ar-purged and FT samples yielded PVP polymers with molecular weights of about $1.6 \times 10^6$ at only 0.01 Mrad. In contrast, the non-degassed samples do not form high molecular weight polymer at this dose. Corresponding higher molecular weights are achieved at higher doses.

EXAMPLE 3

This example illustrates the highly desirable non-Newtonian rheological properties of the PVP solutions useful in this invention. A 10% aqueous NVP solution was degassed by argon gas purging and polymerization was accomplished by gamma-radiation using 0.05 Mrad total dose. This polymer had a mol. wt. greater than 2,000,000 and exhibited the following highly non-Newtonian rheology (greatly reduced viscosity with increasing shear rate). Measurements of viscosity (in centipoise) and shear rate ($sec^{-1}$) were made at 25° C. using a Brookfield HBT/RVT and #51 cone and plate viscometer:

TABLE 4

| | Shear Rate ($Sec^{-1}$) | Viscosity (CPS) |
|---|---|---|
| 16% PVP: | 1.9 | 49,650 |
| | 9.6 | 30,600 |
| | 76.8 | 12,000 |
| | 384.0 | 2,400 |
| 12% PVP: | 1.9 | 31,950 |
| | 9.6 | 10,900 |
| | 76.8 | 5,400 |
| | 384.0 | 2,400 |

EXAMPLE 4

This example illustrates the improved properties of the PVP composition of this invention as an ophthalmic viscoelastic surgical material.

Five healthy female cynomolgus monkeys, 2.5–4.0 kg, determined free of ocular pathology by slit lamp examination were used for the study.

PVP solutions were prepared by gamma irradiation as described in Example 1. Two test solutions were evaluated: (1) "605" - consisted of 10% NVP in distilled $H_2O$ and gamma irradiated to 0.05 Mrad at a distance of 6" (Dose Rate - 93 rads/min) and (2) "805" - a 10% NVP solution in distilled $H_2O$ irradiated to 0.05 Mrad at 8" (Dose Rate - 54 rads/min). After polymerization, the viscous gel-like solutions were autoclave sterilized at 121° C. for 30 minutes. Molecular weights determined by gel permeation chromatography were greater than 1,000,000 for both "605" and "805" samples.

Prior to the procedure, the monkeys were anesthetized by an intramuscular injection of Ketaset 10-15 mg/kg and Rompun 2.5-3.0 mg/kg. An ocular speculum was placed to retract the lids. SLE and IOP measurements were conducted at this point. A 1cc disposable syringe with a 30 g needle was then used to penetrate into the AC and evacuate aqueous humor. The test syringe carrying 0.05 cc of the PVP solution was introduced at the same site, through the cornea into the AC just above and parallel to the iris. One eye of each animal was injected. Monkeys #1, #3, #4 were injected with the "805" PVP solution. Monkeys #2, #5 were injected with the "605" PVP solution.

Slit lamp examinations were carried out at 6, 12, 24, 48 and 72 hours, one week and two weeks after the procedure. IOP was measured by a Shiotz tonometer and by a digital Tonopen at 3, 9, 12, 24, 48 and 72 hours, one week and two weeks after the procedure. For each examination, the monkeys were sedated by I.M. injection of Ketaset 10 mg/kg and 2.5 mg/kg Rompun. The clinical changes were described and/or scored according to the McDonald Shaddock scoring system.

The results of the test are set forth in Table 5 and indicate excellent bioacceptance and no significant post-injection rise in IOP.

TABLE 5

| | | PRE PR | 3H PR | 6H PR | 6H CE | 6H C | 6H F | 9H PR | 12H PR | 1D PR | 1D CE | 1D C | 1D F | 2D PR | 2D CE |
|---|---|---|---|---|---|---|---|---|---|---|---|---|---|---|---|
| 805 OG #1 | R L | 15 | | 6 | 0 | 1 | 1 | 6 | 12 | 8 | 0 | 1 | 1 | 12 | 0 |
| 605 OG #2 | R L | 15 | | 13 | 0 | 1 | 1 | 26 | 18 | 15 | 0 | 1 | 1 | 7 | 0 |
| 805 OG #3 | R L | 15 | 24 | 11 | 0 | 1 | 1 | 13 | 13 | 17 | 0 | 2 | 1 | 10 | 0 |
| 805 OG #4 | R L | 15 | 14 | 13 | 0 | 2 | 1 | 16 | 17 | 17 | 1 | 2 | 1 | 15 | 0 |

TABLE 5-continued

| | | | | | | | | | | | | | | | |
|---|---|---|---|---|---|---|---|---|---|---|---|---|---|---|---|
| 605 | R | | | | | | | | | | | | | | |
| OG #5 | L | 16 | 19 | 20 | 0 | 1 | 0 | 17 | 17 | 17 | 1 | 2 | 1 | 8 | 0 |

| | | 2D | | 3D | | | | 1W | | | | 2W | | | |
|---|---|---|---|---|---|---|---|---|---|---|---|---|---|---|---|
| | | C | F | PR | CE | C | F | PR | CE | C | F | PR | CE | C | F |
| 805 | R | | | | | | | | | | | | | | |
| OG #1 | L | 1 | 1 | 12 | 0 | 1 | 1 | 15 | 0 | 0 | 0 | 15 | 0 | 0 | 0 |
| 605 | R | 2 | 1 | 14 | 0 | 1 | 1 | 12 | 0 | 0 | 0 | 12 | 0 | 0 | 0 |
| OG #2 | L | | | | | | | | | | | | | | |
| 805 | R | | | | | | | | | | | | | | |
| OG #3 | L | 1 | 1 | 10 | 0 | 1 | 0 | 13 | 0 | 0 | 0 | 15 | 0 | 0 | 0 |
| 805 | R | 1 | 1 | 11 | 0 | 1 | 0 | 16 | 0 | 0 | 0 | 16 | 0 | 0 | 0 |
| OG #4 | L | | | | | | | | | | | | | | |
| 605 | R | | | | | | | | | | | | | | |
| OG #5 | L | 2 | 1 | 12 | 0 | 1 | 0 | 17 | 0 | 0 | 0 | 12 | 0 | 0 | 0 |

PR = INTRAOCULAR PRESSURE, CE = CORNEAL EDEMA, C = CELLS, F = FLARE

EXAMPLE 5

This example demonstrates the excellent biocompatibility of the viscoelastic solutions of this invention through tests in rabbit eyes.

A PVP solution was prepared by irradiating a 20% solution of NVP in distilled $H_2O$ to 0.1 Mrad. After polymerization, the solution was autoclaved at 121° C. for 15 minutes for sterilization. It was extremely viscous and gel-like. The molecular weight was greater than 1,000,000.

Six healthy albino rabbits (2.5 –3.5 Kg) determined free of ocular irritation by slit-lamp microscope examination, were used for this study.

Prior to the procedure each rabbit was anesthetized by intramuscular injection of Ketaset (20 mg/kg) and Rompun (15 mg/kg). A topical anesthetic (Tetracaine) and Atropine were instilled in both eyes. An ocular speculum was placed to retract the lids. A 1cc disposable syringe with a 25 g needle was used to evacuate 0.15 ml of aqueous humor. The test syringe with 0.1 ml of the material was introduced through the cornea into the anterior chamber just above and parallel to the iris. As a control, the opposite eye of each rabbit was subjected to a similar procedure and instillation of 0.1 ml of BSS.

Slit lamp examinations were conducted approximately 4 hours, 24 hours, 48 hours, 72 hours and one week after the procedure. Ocular changes were described or scored according to the system of McDonald and Shaddock.

Tonometry by using Schiotz tonometer was carried out just before the procedure and 24 hours, 48 hours, 72 hours and one week after the procedure after anesthetizing with intramuscular injection of Ketaset (20 mg/kg) and Rompun (15 mg/kg) and Tetracaine. Photos were taken at 24 hours, 72 hours and one week after the procedure. After the last examination the eyes were enucleated and subjected to histopathology.

The results are set forth in the following tables and show no post-operative IOP change.

TABLE 6

| | INTRAOCULAR PRESSURE (mm Hg) FOLLOWING 0.1 ml A.C. INJECTION OF PVP VISCOELASTIC SOLUTION | | | | |
|---|---|---|---|---|---|
| Rabbit No. | Before Procedure | 24 Hours | 48 Hours | 72 Hours | One Week |
| #3 | 17 | 16 | 17 | 17 | 17 |
| #4 | 19 | 11 | 15 | 16 | 17 |
| #5 | 19 | 17 | 17 | 16 | 16 |
| #6 | 17 | 17 | 15 | 16 | 15 |
| #7 | 16 | 15 | 16 | 17 | 16 |

TABLE 6-continued

| | INTRAOCULAR PRESSURE (mm Hg) FOLLOWING 0.1 ml A.C. INJECTION OF PVP VISCOELASTIC SOLUTION | | | | |
|---|---|---|---|---|---|
| Rabbit No. | Before Procedure | 24 Hours | 48 Hours | 72 Hours | One Week |
| #8 | 16 | 16 | 16 | 17 | 15 |

Slit lamp examinations at 24 hrs, 48 hrs, 72 hrs and one week after A.C. injection showed normal quiet eyes with no adverse reactions (no corneal edema, no iris vessel engorgement, etc.).

The eyes from the rabbits completing 7 days of follow-up were enucleated and immersed in 40 ml of Trumps fixative and submitted for histopathology. The samples were stored a minimum of 24 hours at 4° C. and then delivered for pathology studies.

Tissue sections were prepared and stained with Hematoxylin and Eosin. Eye sections were evaluated for foreign body and inflammatory reactions as evidenced by foreign body multinucleated giant cells, macrophages, abundance of lymphocytes and other mononuclear inflammatory cells. Several slides from each quadrant of the eye were carefully examined. For all eyes, no evidence or indication of foreign body giant cells or macrophages were seen. The good biocompatibility of the PVP solution was shown by the absence of any foreign body reactions or inflammatory reactions following instillation of 0.1 ml of the 20% aqueous PVP solution prepared by gamma polymerization.

EXAMPLE 6

This example illustrates the use of the viscoelastic PVP compositions of this invention as synthetic vitreous materials and indicates their good biocompatibility as shown by injection into the vitreous of rabbit eyes.

For this vitreous injection evaluation, six New Zealand white rabbits were used. They were anesthetized with 0.8 ml Ketaset and 0.8 ml Rompun given i.m. Following a 3 mm corneal scleral incision, an anterior capsulotomy was performed with phacoemulsification using a Cavitron 8000. The corneal wound was closed with 10/0 prolene sutures. A conjunctival dissection was then performed 3 mm behind the limbus to uncover bare sclera. Using a one ml syringe with a 27 gage needle, penetration 3 mm behind the limbus was made through the sclera so that the posterior lens capsule remained intact. Under direct observation of the needle tip, 0.10–0.15 ml of 10% aqueous PVP, prepared by the method of Example 4, was injected into the vitreous cavity.

Slit lamp examinations of the eyes were carried out daily for four weeks post-operatively. The eyes remained quiet and the retina appeared unchanged in all eyes. The vitreous remained clear and the injected PVP solution was not detectable by slit lamp observation. There was no adverse reaction to the viscoelastic material of this invention in the vitreous.

EXAMPLE 7

This example demonstrates the compatibility of mixtures of the PVP solutions of this invention with viscoelastic solutions of other high molecular weight hydrophilic polymers such as hyaluronic acid (HA) or carboxymethylcellulose (CMC).

A 10% aqueous solution of PVP prepared by gamma radiation polymerization was mixed with a 1.0% solution of HA ("Healon" - commercially available material for clinical use in ophthalmic surgery). The PVP and HA solutions were miscible yielding a homogeneous, clear, viscous, gel-like mixed viscoelastic solution of HA and PVP which is useful for ophthalmic surgical applications. A similar experiment was conducted using mixtures of the PVP solution and a viscoelastic solution of CMC (3.7%, autoclave sterilized, mol. wt. greater than 500,000). The PVP and CMC solutions were miscible yielding clear, homogeneous mixed viscoelastic solutions suitable for ophthalmic applications.

What is claimed is:

1. A composition particularly adapted for use as an ophthalmic viscoelastic surgical material in the anterior or posterior chamber of the eye consisting of an aqueous solution containing at least about 1.5% to about 25%, by weight, of a physiologically acceptable, water-soluble polyvinylpyrrolidone polymer or polyvinylpyrrolidone copolymer, having a molecular weight greater than 500,000, said aqueous solution having a viscosity greater than about 5,000 centipoises, measured at 25° C. using a Brookfield viscometer.

2. The composition of claim 1 wherein said aqueous solution comprises a physiological saline solution of said polyvinylpyrrolidone.

3. The composition of claim 1 wherein said aqueous solution comprises a buffered physiological saline solution of said polyvinylpyrrolidone.

4. The composition of claim 1 wherein said copolymer comprises at least about 50 mol. % N-Vinylpyrrolidone and the comonomer is hydrophilic.

5. The composition of claim 1 wherein said copolymer comprises a copolymer of N-Vinylpyrrolidone and an anionic or cationic comonomer.

6. The composition of claim 1 wherein said solution of polyvinylpyrrolidone has a viscosity in the range of from about 5,000 to about 500,000 cps.

7. The composition of claim 1 additionally containing one or more different viscoelastic material miscible with said polyvinylpyrrolidone solution.

8. The composition of claim 7 wherein said different viscoelastic material is selected from the group consisting of hyaluronic acid, chondroitin sulfate and carboxymethylcellulose.

9. The composition of claim 1 or 7 wherein said compositions are useful as a vitreous replacement or injectable into the vitreous of the eye in an ophthalmic surgical procedure.

10. A composition according to claim 1 wherein said polyvinylpyrrolidone or polyvinylpyrrolidone copolymer is prepared by gamma-irradiation induced polymerization of N-vinylpyrrolidone in a substantially aqueous solution.

11. In an ophthalmic surgical procedure wherein the anterior or posterior chamber of the eye is filled with a viscoelastic space-filling and ocular tissue protective surgical material, the improvement comprising the utilization therein of the composition of claim 1 as said surgical material.

12. An ophthalmic surgical procedure according to claim 11 wherein said surgery comprises intraocular lens implantation.

13. An ophthalmic surgical procedure according to claim 11 wherein said surgery comprises cataract surgery.

14. An ophthalmic surgical procedure according to claim 11 wherein said surgery comprises a corneal transplant.

15. An ophthalmic surgical procedure according to claim 11 wherein said surgery comprises glaucoma surgery.

16. An ophthalmic surgical procedure according to claim 11 wherein said surgery comprises retinal surgery.

17. An ophthalmic surgical procedure according to claim 11 wherein said surgery comprises vitreous replacement.

18. An ophthalmic surgical procedure according to claim 11 wherein said ophthalmic surgical material additionally contains one or more different viscoelastic material miscible with said polyvinylpyrrolidone solution.

19. An ophthalmic surgical procedure according to claim 18 wherein said different viscoelastic material is selected from the group consisting of hyaluronic acid, chondroitin sulfate and carboxymethylcellulose.

* * * * *